US00PP29363P3

(12) United States Plant Patent
Olesen

(10) Patent No.: US PP29,363 P3
(45) Date of Patent: Jun. 12, 2018

(54) MINIATURE ROSE PLANT NAMED 'POULPAR099'

(50) Latin Name: ***Rosa* hybrid**
Varietal Denomination: Poulpar099

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 64 days.

(21) Appl. No.: 15/330,298

(22) Filed: Sep. 6, 2016

(65) Prior Publication Data

US 2018/0070495 P1 Mar. 8, 2018

(51) Int. Cl.
*A01H 5/02* (2006.01)

(52) U.S. Cl.
USPC ..... Plt./118
CPC ..... *A01H 5/0222* (2013.01)

(58) Field of Classification Search
USPC ..... Plt./118
See application file for complete search history.

*Primary Examiner* — Keith O Robinson

(57) ABSTRACT

A new garden rose plant of the Miniature class which has abundant, yellow flowers and attractive foliage. This new and distinct variety has shown to be uniform and stable in the resulting generations from asexual propagation.

3 Drawing Sheets

Botanical designation: *Rosa* hybrid.
Variety denomination: 'Poulpar099'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2011 and the resulting seeds were planted in a controlled environment in Fredensborg, Denmark. The new variety, named 'Poulpar099', originated as a single seedling from the stated cross.

The new variety may be distinguished from its male pollen parent and female seed parent primarily by the following characteristics. The male pollen parent plant attains a growth height of 35 cm in one season, while the new variety grows to 25 cm in one season. The female seed parent plant has orange blend flowers, while the new variety has yellow flowers.

The objective of the hybridization of this rose variety was to create a new and distinct variety for garden use with unique qualities, such as:

1. Uniform and abundant yellow flowers;
2. Vigorous, but compact growth when propagated on its own roots;
3. Exceptional disease resistance.

This combination of qualities is not present in previously available commercial cultivars of this type, known to the inventor, and distinguish 'Poulpar099' from all other varieties of which we are aware.

As part of the rose development program, Mogens N. Olesen germinated the seeds from the aforementioned hybridization during winter of 2011 and conducted evaluations on the resulting seedlings in a controlled environment in Fredensborg, Denmark. 'Poulpar099' was selected in the spring of 2012 by the inventor as a single plant from the progeny of the aforementioned hybridization.

Asexual reproduction of 'Poulpar099' by rooted cuttings was first done by Mogens N. Olesen in the nursery in Fredensborg, Denmark in July, 2012. This initial and other subsequent asexual propagations conducted in controlled environments have demonstrated that the characteristics of 'Poulpar099' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpar099'.

Specifically illustrated in FIG. 1 of the drawing is an open flower above view, flower petals detached, flower buds upon opening, sepals detached, reproductive flower parts, and an unopened flower bud attached to the stem.

DETAILED DESCRIPTION OF THE VARIETY

Figure 1:
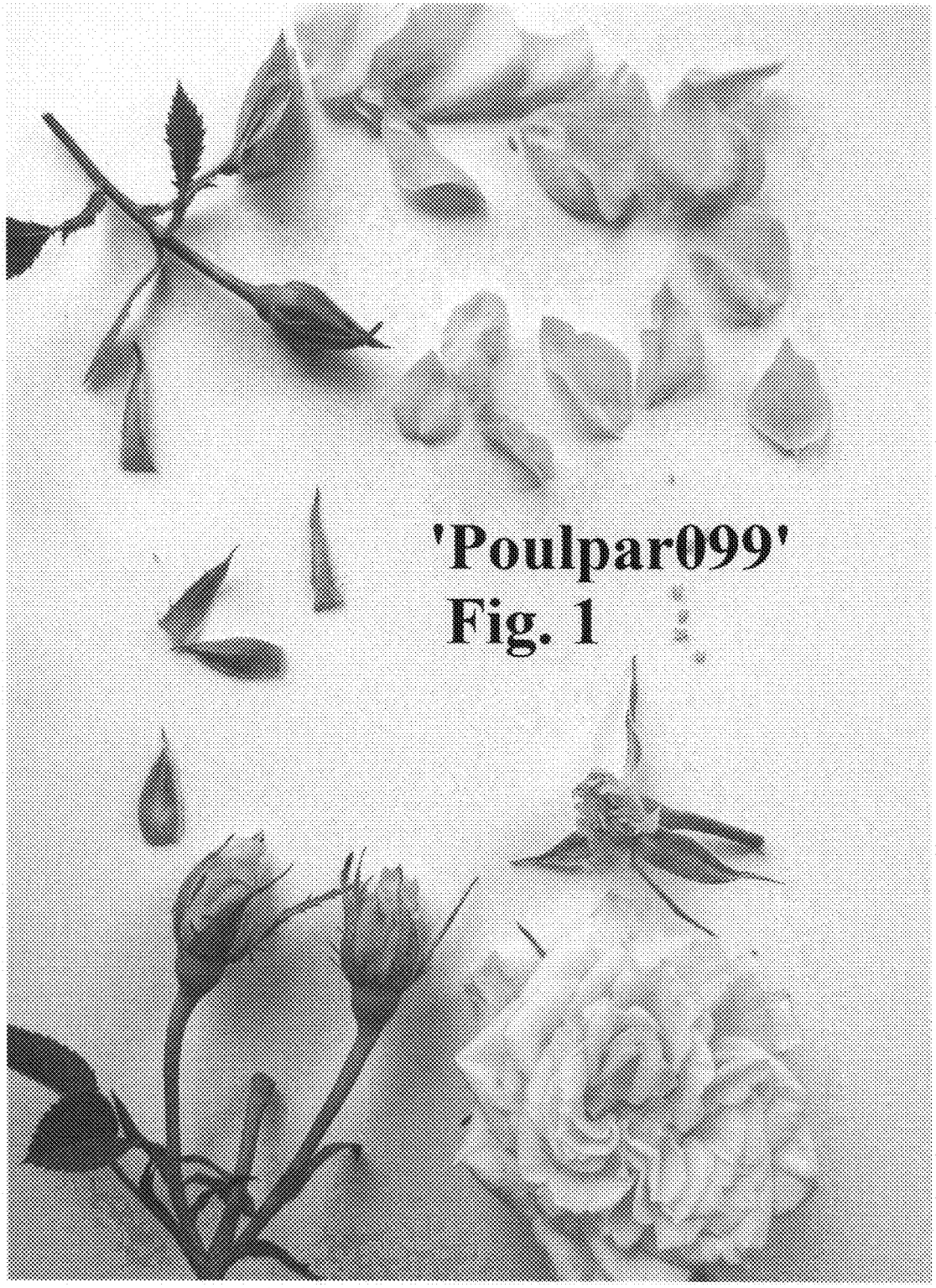
Figure 2:
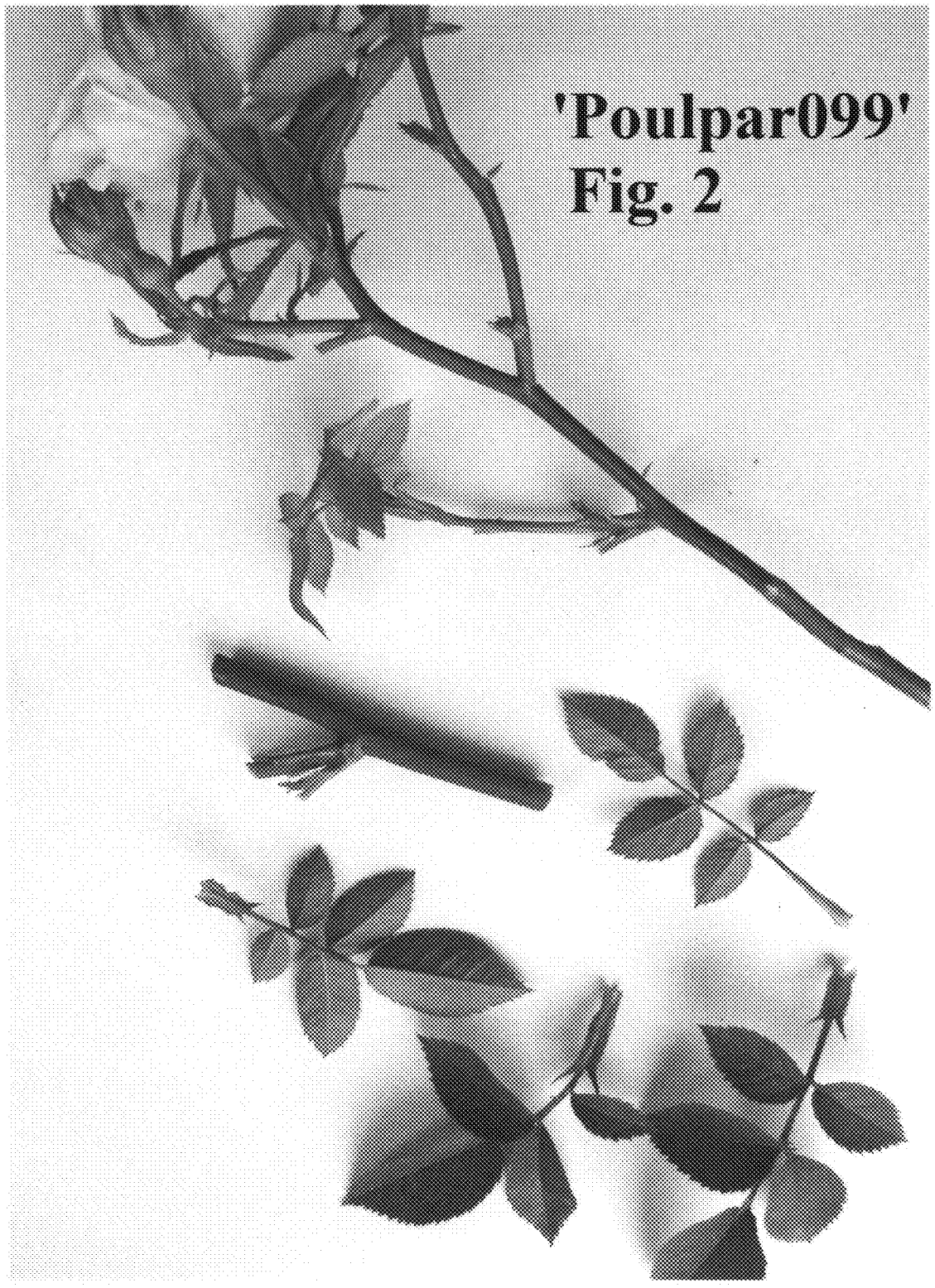
FIG. 2 shows leaves, bare stems, and a cluster of flowers on a branch.
Figure 3:
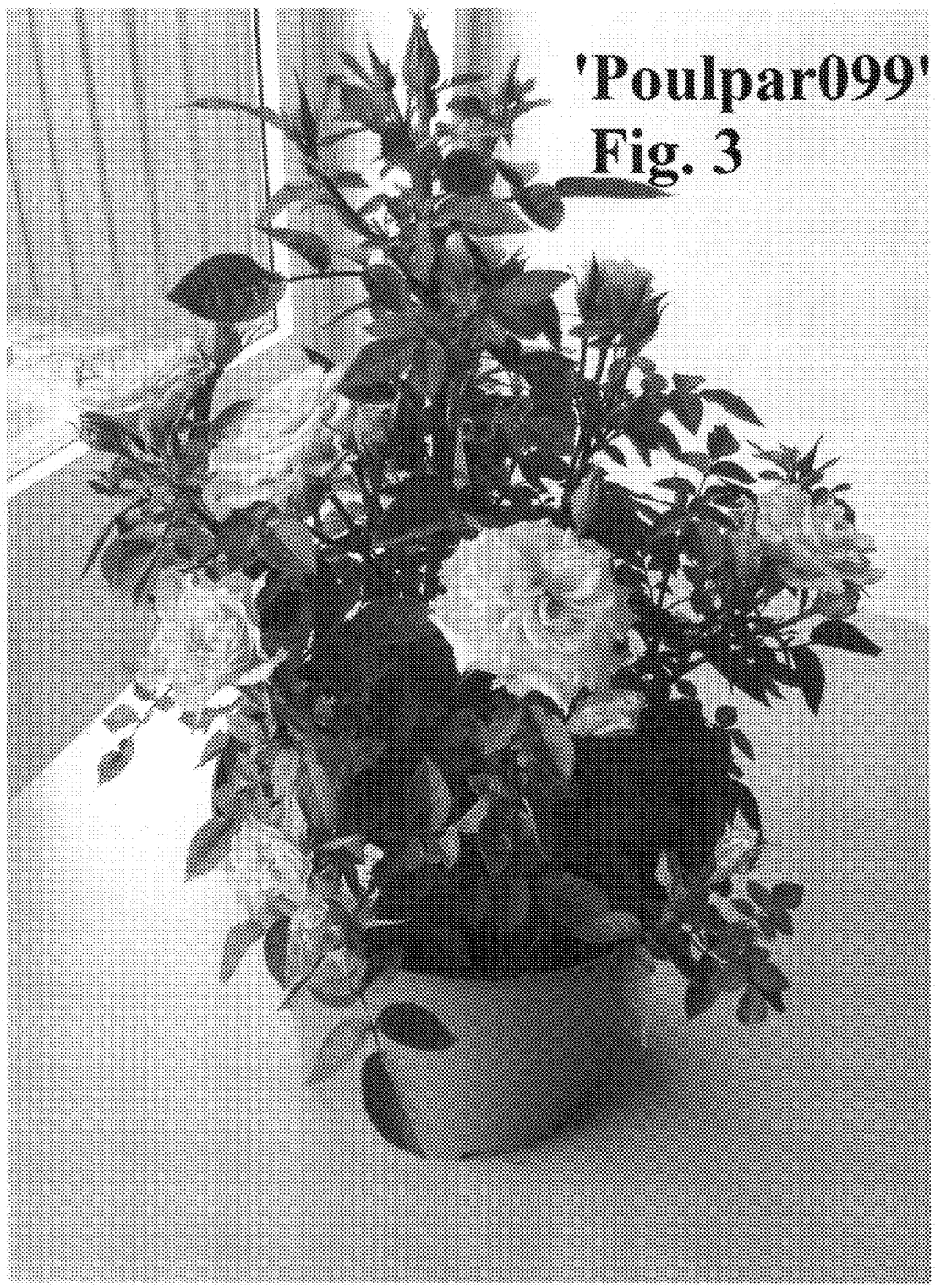
FIG. 3 shows the entire plant in flower growing in a 21 cm container. Plants shown are 1 year old.

The following is a description of 'Poulpar099', as observed in its growth in a container nursery in Odense Denmark. Observed plants are 1 year of age, and were grown on their own roots in 21 cm pots. Color references are made using The Royal Horticultural Society (London, England) Colour Chart, 2001, except where common terms of color are used.

For a comparison, several physical characteristics of the rose variety 'Poulmist', U.S. Plant Pat. No. 18,975 are compared to 'Poulpar099' in Chart 1.

CHART 1

| | 'PouLpar099' | 'Poulmist' |
|---|---|---|
| Petal Count | 50 | 35 to 40 |
| Flower Diameter | 70 mm | 40 mm |
| General Tonality of Flower Color | Yellow-Orange Group 21B | Yellow Group 12B |

FLOWER AND FLOWER BUD

Blooming habit: Continuous.

Flower bud:

*Size*.—Upon opening, 27 mm in length from base of receptacle to end of bud. Bud diameter is 12 mm.

*Bud form*.—Ovoid.

*Bud color*.—As sepals divide petals are Orange-Red Group 34C.

*Sepal inner surface*.—Color: Green Group 139D. Surface: Lightly pubescent.

*Sepal outer surface*.—Color: Green Group 138A with intonations of Red-Purple Group 58A. Texture: Smooth.

*Sepal shape*.—Apex: Cirrhose. Base: Flat at union with receptacle.

*Sepal margin*.—Margins have weak foliaceous appendages on three of the five sepals.

*Sepal size*.—18 to 22 mm long, 4 to 6 mm wide.

*Receptacle*.—Texture: Smooth. Size: 5 mm in height, 7 mm wide. Color: Yellow-Green Group 146A. Shape: Campanulate.

*Pedicel*.—Surface: Smooth. Length: 20 to 30 mm. Diameter: 2 to 3mm on average. Color: Yellow-Green Group 146C. Strength: Moderate.

*Peduncle*.—Length: 30 to 80 mm. Diameter: About 3 mm. Color: Yellow-Green Group 146A with intonations of Greyed-Orange Group 176A. Texture: Smooth.

Flower bud development: Flower buds are borne in clusters of 3 to 5 flower buds per stem. Development as a corymb.

Flower bloom:

*Fragrance*.—None.

*Duration*.—The blooms have a duration on the plant of approximately 15 days. Petal drop not easy.

*Size*.—Flower diameter is about 70 mm when open. Flower depth is 20 mm.

*Flower shape*.—Rosette, very double flower with many slightly overlapping petals of different sizes.

*Shape of flower, side view*.—The upper portion is flat. The lower portion is flat and convex.

Petalage: Under normal conditions, flowers have about 50 petals.

General tonality of flower: Open flowers are Yellow-Orange Group 21B.

Petal color:

*Upon opening, outer petals*.—Upper surface: Yellow-Orange Group 15C. Lower surface: Yellow-Orange Group 15C with occasional light intonations of Orange-Red Group 34C.

*Upon opening, inner petals*.—Upper surface: Yellow-Orange Group 15C. Lower surface: Yellow-Orange Group 15C.

*Basal petal spots, upon opening*.—Upper surface: Yellow-Orange Group 15B. Lower surface: Yellow-Orange Group 15B.

*After opening, outer petals*.—Upper surface: Yellow-Orange Group 14C. Lower surface: Yellow-Orange Group 14C.

*After opening, inner petals*.—Upper surface: Yellow-Orange Group 14C. Lower surface: Yellow-Orange Group 14C.

*Basal petal spots, after opening*.—Upper surface: Yellow-Orange Group 14B. Lower surface: Yellow-Orange Group 14B.

Petals:

*Petal reflex*.—Somewhat reflexed.

*Margin*.—Entire and uniform. Moderate undulations. Occasional point at center and cleft.

*Shape*.—Broad elliptic. Apex shape: Rounded and cuspidate. Base shape: Round.

*Size*.—20 mm (l)×35 mm (w).

*Texture*.—Smooth.

*Thickness*.—Average.

Petaloids:

*Size*.—15 mm (l) by 8 mm (w).

*Quantity*.—About 10. Shape: Irregular, asymmetric, elliptic, with an acute base and apex.

*Color*.—Yellow-Orange Group 14C on the upper and lower surface.

Reproductive flower parts:

*Pollen*.—None observed.

*Anthers*.—Size: 2 mm in length. Color: Yellow-Orange Group 14A. Quantity: 80 on average.

*Filaments*.—Color: Yellow-Orange Group 14A. Length: 5 mm.

*Pistils*.—Length: 50 mm. Quantity: 3 on average.

*Stigmas*.—Color: Greyed-Yellow Group 160A.

*Styles*.—Color: Red Group 49A.

*Location of stigmas*.—Level in location relative to the length of the filaments and the height of the anthers.

*Hips*.—None Observed.

PLANT

Plant growth: Upright, bushy. Plants are 25 cm in height, and 30 cm wide.

Stems:

*Color*.—Juvenile growth: Yellow-Green Group 146B. Mature growth: Yellow-Green Group 146A with intonations of Greyed-Red Group 177A.

*Length*.—On average, canes are 20 cm from the base of the plant to the flowering portion.

*Diameter*.—4 to 7 mm.

*Internodes*.—On mature canes about 20 mm between nodes.

*Surface texture*.—Young wood: Smooth. Older wood: Smooth.

Long prickles: None observed.

Plant foliage:

*Compound leaf*.—65 to 90 mm (l)×40 to 55 (w).

*Quantity*.—4 leaves per 10 cm of stem on average.

*Leaf bearing angle to the stem*.—45 degrees.

*Color of juvenile foliage*.—Upper side: Yellow-Green Group 137B. Lower side: Yellow-Green Group 147C. Anthocyanin: Generalized throughout, Greyed-Red Group 179A.

*Color of mature foliage*.—Upper side: Yellow-Green Group 147A. Lower side: Yellow-Green Group 147C.

Plant leaves and leaflets:

*Stipules*.—Size: 15 mm long, 4 mm wide. Quantity: 2 per compound leaf. Shape: Linear, slightly broad based with outward extending apices. Margins: Finely serrated with many stipitate glands. Color: Yellow-Green Group 147B with intonations of Greyed-Red Group 178D.

*Petiole*.—Length: Up to 12 mm. Diameter: About 2 mm.

*Upper surface*.—Color: Yellow-Green Group 147B.

*Lower surface*.—Color: Yellow-Green Group 144A.

*Rachis*.—Length: About 12 mm.

*Upper surface*.—Color: Yellow-Green Group 147B.

*Lower surface*.—Color: Yellow-Green Group 144A.

*Leaflet*.—Quantity: Normally 5 leaflets. Margins: Serrulate. Size: On average terminal leaflets are 30 to 40 mm long, 15 to 25 mm wide. Shape: Generally elliptical. Base: Rounded. Apex: Acuminate. Texture: Smooth. Thickness: Average. Arrangement: Odd pinnate. Venation: Reticulate. Glossiness: Not glossy.

Disease resistance: Above average resistance to powdery mildew *Sphaerotheca pannosa*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Miniature rose class named 'Poulpar099', substantially as illustrated and described herein, due to its abundant yellow flowers, disease resistance, and extended period of bloom.

* * * * *

'Poulpar099'

'Poulpar099'